United States Patent [19]
Karwoski et al.

[11] Patent Number: 5,824,050
[45] Date of Patent: Oct. 20, 1998

[54] PROSTHESIS WITH IN-WALL MODULATION

[75] Inventors: Theodore Karwoski, Hudson; Paul Martakos, Pelham, both of N.H.; Peter Gingras, Bedford, Mass.; Steve A. Herweck, Nashua; Tom Swanick, Mont Vernon, both of N.H.

[73] Assignee: Atrium Medical Corporation, Hudson, N.H.

[21] Appl. No.: 760,115

[22] Filed: Dec. 3, 1996

[51] Int. Cl.⁶ .................................. A61F 2/06; A61F 2/04
[52] U.S. Cl. .................................. 623/1; 623/11; 623/12
[58] Field of Search .................................. 623/1, 11, 12; 600/36; 606/151–158, 194, 195

[56] References Cited

U.S. PATENT DOCUMENTS

| | | | |
|---|---|---|---|
| 4,629,458 | 12/1986 | Pinchuk | 623/1 |
| 4,955,899 | 9/1990 | Della Corna et al. | 623/1 |
| 5,028,597 | 7/1991 | Kodama et al. | 514/56 |
| 5,061,276 | 10/1991 | Tu et al. | 623/1 |
| 5,123,917 | 6/1992 | Lee | 623/1 |
| 5,152,782 | 10/1992 | Kowligi et al. | 623/1 |
| 5,163,951 | 11/1992 | Pinchuk et al. | 623/1 |
| 5,229,045 | 7/1993 | Soldani | 264/41 |
| 5,354,329 | 10/1994 | Whalen | 623/1 |
| 5,413,597 | 5/1995 | Krajicek | 623/1 |
| 5,453,278 | 9/1995 | Chan et al. | 424/422 |

FOREIGN PATENT DOCUMENTS

| | | | |
|---|---|---|---|
| 9505277 | 2/1995 | WIPO | 623/1 |
| 9505555 | 2/1995 | WIPO | 623/1 |

*Primary Examiner*—Debra S. Brittingham
*Attorney, Agent, or Firm*—Lahive & Cockfield, LLP

[57] ABSTRACT

The wall of a prosthesis has a region which modulates communication through the porosity of the wall. The prosthesis is unitary, but may be assembled in successive bodies which are coalesced, so that the porous microstructure changes distinctly at stages through the thickness dimension of the wall. One embodiment is formed entirely of fluoropolymer, and has at least one surface adapted to support tissue regeneration and ingrowth. The modulation region is a stratum of high water entry pressure that reduces pulsatile hydraulic pressure transmission, or locally alters fluid-born-distribution of biological material through the wall and allows more natural gradients for tissue regeneration and growth in the outer region of the wall.

11 Claims, 6 Drawing Sheets

PROSTHESIS WITH IN-WALL MODULATION

REFERENCE TO RELATED PATENTS AND PATENT APPLICATIONS

This application relates to the commonly owned U.S. patent applications having the following titles and attorney docket numbers, which are being filed by applicant of even date herewith: VASCULAR ENDOPROSTHESIS AND METHOD, Attorney Docket ATA-127; MULTI-STAGE PROSTHESIS, Attorney Docket ATA-140; EXPANDABLE SHIELDED VESSEL SUPPORT, Attorney Docket ATA-148. It also relates to applicants' earlier U.S. Pat. Nos. 5,433,909 and 5,474,824. The foregoing patents describe methods of making extruded PTFE material having large oriented nodes, uniaxially oriented fibrils and a pore structure of oriented channels that differs at different surfaces, or that varies along the thickness dimension. The aforesaid patent applications each describe constructions or methods of use for prostheses, which are further useful in the embodiments and applications of the present invention. Each of the aforementioned U.S. patents and patent applications is hereby incorporated by reference herein in its entirety.

BACKGROUND

This invention relates to a lamellate polytetrafluoroethylene material that can be formed into an implant where there is an improvement in the surgical handling accompanied with enhanced healing properties due to the novel arrangement of variable porosity regions of polytetrafluoroethylene. This invention relates to materials utilized in the production of devices for in vivo implantation, such as heart valve leaflets, sutures, vascular access devices or any related products, but more particularly relates to vascular grafts, for example, to porous polytetrafluoroethylene prostheses intended for placement or implantation to supplement or replace a segment of a natural, biological blood vessel. It also relates to patches or supports for tissue repair or reinforcement. For simplicity of exposition below, the invention will be discussed solely with relation to an implantable vascular graft, or a liner for a vessel which might, for example, be delivered intraluminally.

Reference is made to commonly-owned U.S. Pat. Nos. 5,433,909 and 5,474,824 which disclose a method and a product made thereby which is an extruded tube of polytetrafluoroethylene having a tailored porosity. The tube is made by extrusion, of a perform having differently-prepared PTFE paste at two or more levels along its radial section, followed by stretching and generally also sintering so as to achieve the desired strength and pore structure in the final product. As described in those patents and elsewhere, porosity may be tailored to achieve certain desirable properties in the structure of nodes and fibrils that affect permeability and various forms of tissue compatibility, such as the promotion or prevention of tissue growth. In particular, the above patents describe a method of fabricating tubes of PTFE material having good mechanical strength, together with a combination of other features including one or more of a large reticulated node structure which enhances tissue growth, a small pore structure which limits weeping of the graft, and different porosities through the thickness portion of the tube wall to achieve desired properties at both surfaces. The aforesaid commonly-owned patents also describe a method of obtaining these properties in a single PTFE tube in which a property such as lubrication level has been consciously made non-uniform.

Other approaches to extruding a porous PTFE tube have involved stacking two preforms of different PTFE materials, or PTFE and a dissimilar material, together and extruding a layered structure.

Still other approaches to incorporating PTFE as the sole or a large portion of a vascular graft have involved numerous constructions. These include constructions wherein an inner tube is surrounded by one or more other layers of tubing, foam or fiber wrapping to enhance its mechanical compliance and, for example, provide direct impermeability, or result in clotting which, after a short time, becomes impermeable. The inner tube is generally formed of PTFE, selected for its highly advantageous biocompatibility properties in the blood path. Various outer layers may consist of fibers either helically wound or electrostatically flocced, films of thin material, tape wrap generally also of thin material, or coatings. Materials used for these layers may also include impermeable polyurethane or other soluble polymer coatings, emulsions and also PTFE films.

These composite structures are in some ways similar to the earlier generation of fabric grafts made of woven or knitted Dacron or the like, and each represents an attempt to address or optimize some of the various constraints encountered in trying to replace a vessel with material which is strong, capable of long term patency and has some degree of tissue compatibility.

In general, however, conventional vascular grafts manufactured from porous polytetrafluoroethylene have limitations in surgical handling and healing.

Presently, many vascular grafts exhibit some degree of weeping or blood loss during implantation. A variety of factors effect this surgical complication, one being prewetting of vascular grafts with heparinized saline or antibiotics to render the surface thrombus and infection resistant. Prewetting of the graft results in a reduction of the hydrophobic properties with an effective increase in permeability. Cohesion of platelets and adhesion of fibrin in the graft wall can initiate the coagulation cascade resulting in thrombus formation. The thrombi are responsible for the formation of emboli in tubular prosthesis with small diameters.

Native arteries and veins have a common pattern of organization made up of three layers: an internal intima, surrounded by a media, and then an external adventitia. Each of these layers has a predominant structure and cell-type. The walls of arteries are built of elastin, collagen, a non-fibrous glucosaminoglycan-rich matrix and smooth muscle cells. The microscopic structure of the artery wall correlates with the function of the various wall-layers and components.

Several studies support the belief that there is a net transport of macromolecules across the arterial wall. The transport process is controlled by diffusion, convention, and forces. Convection is associated with the hydraulic flux resulting from pressure or osmotic differences across the arterial wall. Diffusion occurs in response to a concentration driving force.

While a number of vascular grafts, or processes for preparing the same, provide for a stronger graft, such grafts do not generally possess a differential permeability effective to achieve enhanced healing and tissue ingrowth, and at the same time offer improved surgical handling.

There is a need for an in vivo implantable material device, and in particular vascular grafts which are formed as a lamellate structure that mimics the natural artery with differential cross-section permeability composed of collagen and elastin and is acceptable to the surrounding tissue.

It remains desirable to provide prostheses or material having enhanced tissue compatibility or long term patency or growth compatibility characteristics.

SUMMARY OF THE INVENTION

This is achieved in accordance with the present invention by providing an implantable or prosthetic material with at least first, second and third regions through the wall thickness extending continuously along the length and width thereof, and wherein material of the innermost and outermost regions has a cellular compatibility property such as node size or reticulation structure, while at least one, preferably an interior, region of the wall modulates hydraulic pressure otherwise passing through the porosity of the prosthesis. The first, second and third regions join or merge continuously together along their bounding surfaces, and form a unitary wall.

The products comprising the instant invention have a very broad application in medical devices, such as vascular grafts, endovascular devices, vascular access devices, transcutaneous access devices, synthetic heart valve leaflets, artificial organ implants, etc. In a preferred embodiment, each cross-section region of the implant can be distinguished from other regions by having different pore size, pore shape and porosity. Indeed, the fibril-nodal microstructure throughout the matrix may have the internodal distance, i.e, pore size, in one section at least two to twenty times that for its adjacent sections. An in vivo material having three cross-section regions, for example, the internodal distance of the pores of luminal surface of PTFE vascular graft is about 20 or 30 microns with a corresponding WEP of 200 mm Hg and a specific node/fibril geometry. The internodal distance of the pores of the next zone comprise a range from about 1 to about 10 microns with a corresponding WEP of 400 mm Hg or greater and a specific node/fibril geometry, preferably about 5 to 10 microns. The pore size is excellent for cell growth mediator permeability, as distinguished, for example from total impermeability which causes an undesirable state of encapsulation. Another embodiment of the present invention includes a luminal, second, and third zone of material as previously described whereby the third zone has a pore size range of 50 to 500 microns with a corresponding WEP of 100 mm Hg or less and a specific node/fibril geometry, preferably with an internodal distance of about 50 to 100, to effectively promote fibroblast tissue ingrowth, as the healing process progresses. The lamellate structure of the present invention offers a wall architecture similar in nature to that of a native vessel which contains an intima, media, and adventitia.

A further embodiment of the present invention includes in vivo implantable material as described above in the form of a sheet, tube or enclosure comprising a luminal, a second and a third region as previously described. Another embodiment of the present invention includes the luminal, second and third region of material as previously described with the third region being filled to provide a source location for drug delivery.

For a vascular prosthesis, the outer wall may have a porosity or regular structure of channels which is compatible with and serves as a microscaffolding structure for the growth of connective tissue. The inner face of the prosthesis on the other hand may have a smaller pore structure, optimized for attachment of a neointima for reconstituting a natural biological flow surface at the interior of the vessel. The modulation region serves the function of blocking the direct or immediate transmission of hydrostatic pressure or fluid migration through the thickness dimension of the wall, and prevents through-growth of tissue, allowing a stratification of tissue layers to redevelop over time in a more natural fashion after the prosthesis has been implanted. Pore structure of the modulation region may be irregular, and generally is either small in size, or tortuous in path. The modulation region may also have non-existent porosity, i.e., be a continuous solid.

The prosthesis may be constructed from plural layers or tubes of material by radially nesting a first, second and third layer of material, either as tubes, wound sheets or a wrap and then coalescing the three separate bodies together into a continuous wall body in which each region through the thickness retains the structure of the starting material for that region. Preferably, the entire structure is made from PTFE, or PTFE with another fluoropolymer.

BRIEF DESCRIPTION OF THE DRAWINGS

These and other features of the invention will be understood from the figures herein wherein.

DETAILED DESCRIPTION

Figure 10:
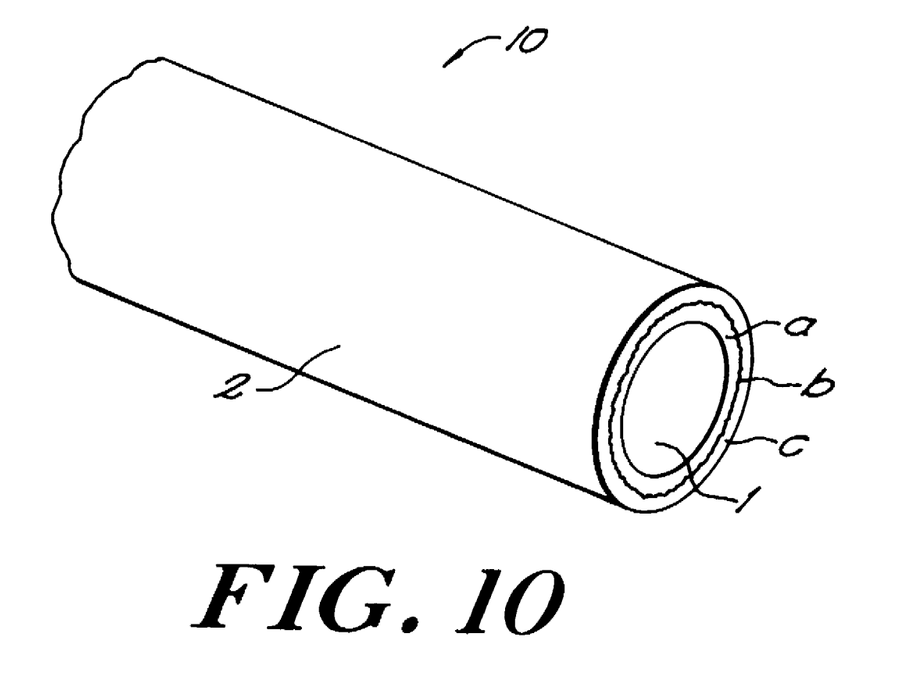
FIG. 10 shows a vascular prosthesis according to any of the above embodiments of the present invention.

FIG. 10 illustrates an implantable prosthetic member 10 according to the present invention, which, is shown in the figure as a tubular member, suitable for implantation as a vascular graft. The member 10 has an inner wall 1 and an outer wall 2 with a thickness dimension extending therebetween. As further illustrated in FIG. 10, there are at least three continuous regions adjacent to each other and extending along the entire area of the member namely, regions a, b and c, illustratively shown in the Figure as concentric strata from the inside to the outside. As described in more detail below, the successive regions a, b, c are not separate structures but are portions of the same wall, and are distinguished by their structural properties as relates in particular to aspects of porosity.

In general, each embodiment of the invention includes at least one region having a zero or sufficiently low porosity that it effectively acts as a barrier to fluid penetration or a barrier which modulates transmission of hydraulic pressure pulsation through the thin wall of the prosthesis. This barrier region may be a completely pore-free stratum, a stratum having small pore size, or a stratum having a high density of crossed, irregular, dead end, or closed cell pores such that it carries out its modulation or barrier function. In the latter case, even large pore material may be used, but its water entry pressure (WEP) is high. This stratum may exist at the region of inner surface 1, the region of outer surface 2, or an intermediate stratum as shown by the position of region b in FIG. 10.

In material science, there is a distinction between material porosity and permeability. Porosity is a direct measure of the physical void volume contained with a boundary, whereas permeability refers to the accessibility of that void volume. Permeability is usually expressed as a rate of flow of liquid or gas per unit area, as a function of differential pressure.

In a porous, fibrous material, that part of the total porosity which is available to fluid flow is also called the "effective porosity." The pressure required to force a liquid into a pore is a function of pore size and geometry, liquid surface tension, and solid/liquid contact angle. Surface tension opposes the entry of any nonwetting liquid into a pore, and this opposition may be overcome by external pressure.

Expanded PTFE material is characterized by lengthwise-oriented fibrils interrupted by transverse nodes. The pore size in microns is typically determined by measuring fiber length between the nodes (internodal distance). To compute fibril length, the material is viewed under sufficient magnification. A fibril length is measured from one edge of one node to the edge of an adjacent node. Fibril lengths are measured from the sample to compute a mean fibril length.

Nodes and fibrils may be further characterized by their relative geometry. That is, nodes by length, width, and height; and fibrils, by diameter and length. It is the relative geometry of nodes to fibrils, as well as, internodal distance that determines porosity and permeability of porous PTFE.

Permeability to fluid flow can be determined by measuring the amount of pressure required for water to permeate the pores of the material. To compute water entry pressure (WEP) one subjects the material to an incrementally increasing water pressure until small beads of water appear on the surface. WEP is a gage which can be used to equate porosity to permeability.

Vascular graft porosity is a measure of the void fraction within the prosthesis wall and is believed to give a rough prediction of the capacity of the graft to anchor newly formed surrounding tissue after implantation, whereas permeability is associated with fluid flow through the graft wall.

Vascular permeability or hydraulic conductivity is related to material porosity. WEP is a good measuring technique to assess this trait because it closely mimics the permeation process at the blood/prosthesis interface. WEP is defined as the pressure value necessary to push water into the pores of a synthetic tubular substrate and can be classified as: High (>400 mm Hg), Medium (200–400 mm Hg), and Low (<200 mm Hg).

It has been widely accepted since the nineteenth century that the hydrostatic pressure difference across the arterial wall is capable of transporting water from the blood into the surrounding interstitial space. The view has long been held that a continuous transport of material occurs across the arterial wall, from its inner to its outer surface. Solutes flow past the endothelium gradually passing through the various arterial wall layers eventually being transferred to the lymphatics or adventitia.

The filtration coefficients of the wall are dependent on the hydraulic conductivity of both the intima and media. The artery wall is a heterogeneous porous medium in which interstitial fluid can flow through the interstices between cells and tissue mimicking a semipermeable membrane with hydrostatic and osmotic pressure components. The osmotic pressure difference across the vessel wall is assumed to be small compared with the hydrostatic pressure or hydraulic conductivity.

More controlled healing and tissue ingrowth is achieved by providing a specific region (outer) for cell penetration, followed by a region (barrier) that does not allow free cellular penetration/permeation but instead, allows the transport of plasma solutes such as cellular mediators (proteins, growth factors, etc.) This barrier minimizes the relatively large hydraulic force present in arterial transport that retards tissue ingrowth. Reports have shown that a negative pressure exists within the perigraft space, while blood components (cells, particles, etc.) are isolated to the blood side of the device.

A vascular graft formed from the lamellate structure of the invention mimics the natural artery with a cross-section that offers differential permeability properties resulting in a healing response acceptable to the surrounding tissue.

In a prototype embodiment of the invention, a prosthesis 10 as described above was fabricated in a multi-step procedure by assembling three physically separate bodies of material together in successive strata and then joining or coalescing them into a single unit.

When a vascular prosthesis is fabricated according to this method, preferably at least one of the bodies is a tube which may, for example, be an axially-stretched tube having a porous structure of internodal space oriented transverse to its surface. Advantageously, the nodal spacing, orientation or structure of successive strata may be offset, non-matching or misaligned to introduce or enhance a barrier or hydraulic modulation effect. For example, a prosthesis may be formed by placing a first PTFE tube on a mandrel, wrapping a ribbon of PTFE in an overlapped or non-overlapped spiral winding over the tube outer surface, and then placing another PTFE tube over the assembly. For this construction, the outermost tube has preferably been previously radially expanded. Heat is then applied to the assembly, optionally with a radial compressive force, to shrink back the outer tube and coalesce the three separate bodies together into a unitary prosthesis. Although effectively "welded" together, there are no visible deformations, and the throughwall properties change abruptly at the interface of each stratum or region with the next.

EXAMPLE 1

PTFE resin (Fluon CD-123 obtained from ICI Americas) was blended with 100 grams of "Isopar H odorless solvent (produced by Exxon Corporation) per pound of PTFE, compressed into a preform billet and extruded into a 3.5 mm I.D. and 4.0 mm O.D. tube in a ram extruder having a reduction ratio of about 200:1 in cross-sectional area from billet to extruded tube. After removal of lubricant, the extruded tube was expanded and sintered, according to the method described in U.S. Pat. Nos. 5,433,909 and 5,474,824, which patents are hereby incorporated by reference herein in their entirety, under various conditions to produce material with different hydraulic porosities. This produced three different tubes, denoted A, B and C, which were used as starting materials for the constructions described below.

Stretch conditions and resultant hydraulic porosities are given below in Table 1.

TABLE 1

|  | Temp (°C.) | Expansion Rate (in/sec) | Ratio (%) | Hydraulic Porosity WEP (mm Hg) |
|---|---|---|---|---|
| (A) | 320 | .004 | 3:1 | 100 |
| (B) | 300 | .018 | 3:1 | 200 |
| (C) | 250 | 7.5 | 2.5:1 | 600 |

Figure 1:
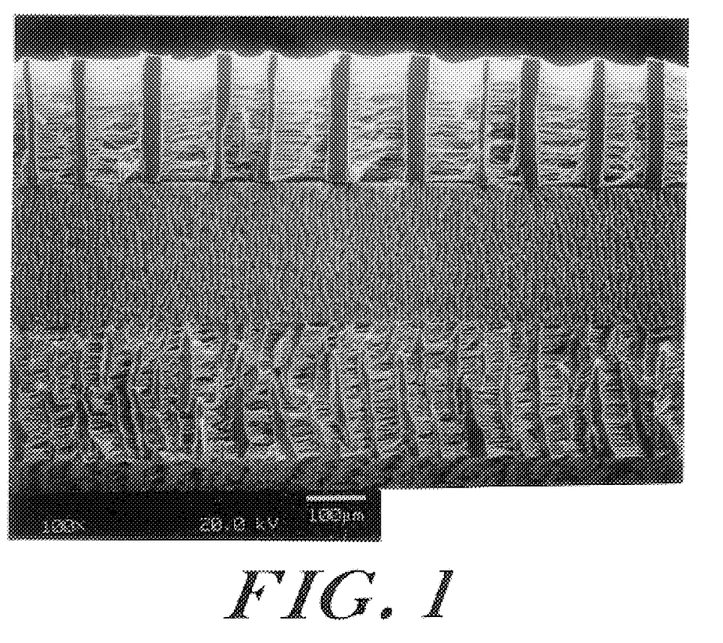
FIG. 1 is a cross-sectional image through a wall of a first embodiment of the invention.

Material (B) was radially expanded to a 4 mm ID on a stainless steel forming mandrel, covered with material C that had been previously dilated to a 5 mm ID, restrained to prevent longitudinal shrinkage, and transferred to an oven at 360° C. for 5 minutes, to prepare a primary lamellate. The primary lamellate was removed from the oven and allowed to cool, covered with material (A) that had been previously dilated to a 5 mm ID, restrained to prevent longitudinal shrinkage, and placed in an oven at 360° C. for 10 minutes, to prepare a final lamellate structure (material B/C/A), a cross-section of which is shown in FIG. 1.

Figure 2:
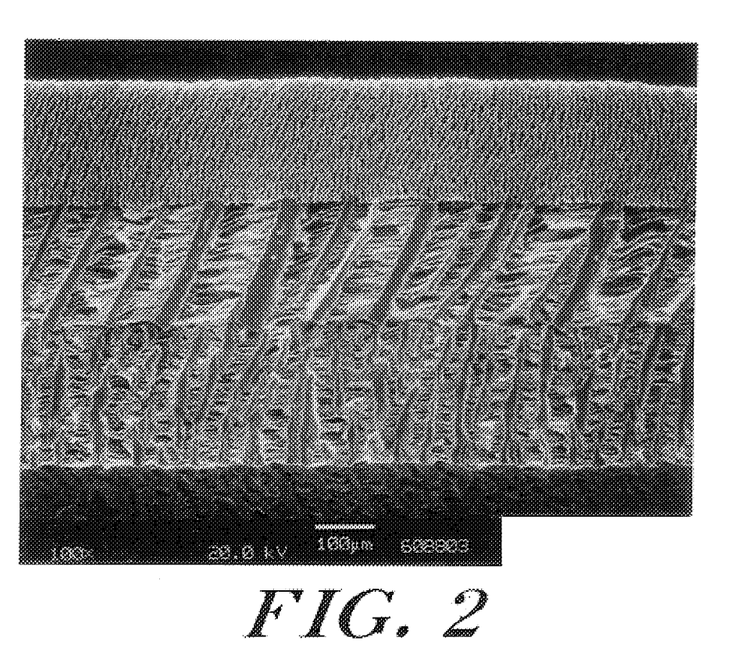
FIG. 2 is a cross-sectional image through a wall of a second embodiment of the invention.

Material (B) was radially expanded to a 4 mm ID on a stainless steel forming mandrel, covered with material (A) that had been previously dilated to a 5 mm ID, restrained to prevent longitudinal shrinkage, and transferred to an oven at 360° C. for 5 minutes, to prepare a primary lamellate. The primary lamellate was removed from the oven and allowed to cool, covered with material C that had been previously dilated to a 5 mm ID, restrained to prevent longitudinal shrinkage, and placed in an oven at 360° C. for 10 minutes, to prepare a final lamellate structure (material B/A/C), a cross-section of which is shown in FIG. 2.

Figure 3:
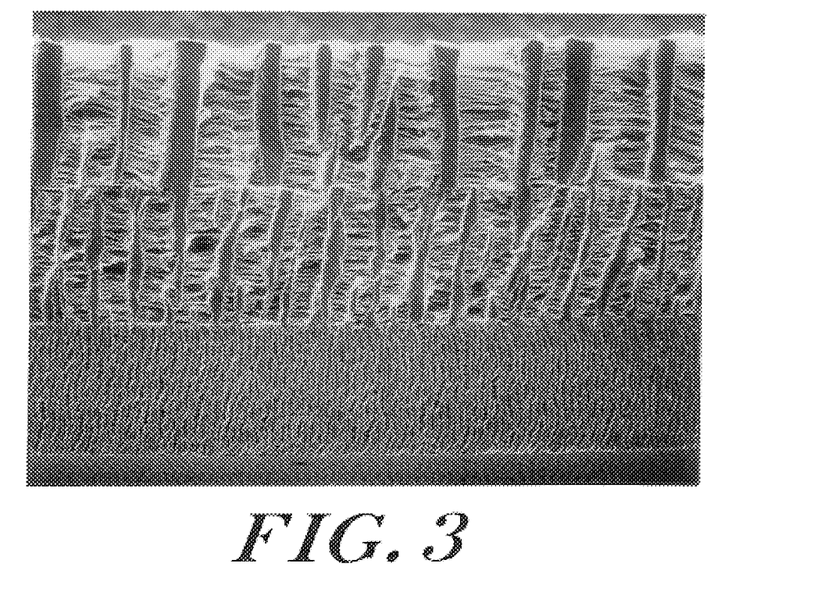
FIG. 3 is a cross-sectional image through a wall of a third embodiment of the invention.

Material C was radially expanded to a 4 mm ID on a stainless steel forming mandrel, covered with material (B) that had been previously dilated to a 5 mm ID, restrained to prevent longitudinal shrinkage, and transferred to an oven at 360° C. for 5 minutes, to prepare a primary lamellate. The primary lamellate was removed from the oven and allowed to cool, covered with material (A) that had been previously dilated to a 5 mm ID, restrained to prevent longitudinal shrinkage, and placed in an oven at 360° C. for 10 minutes, to prepare a final lamellate structure (material C/B/A) a cross-section of which is shown in FIG. 3.

EXAMPLE 2

Figure 4:
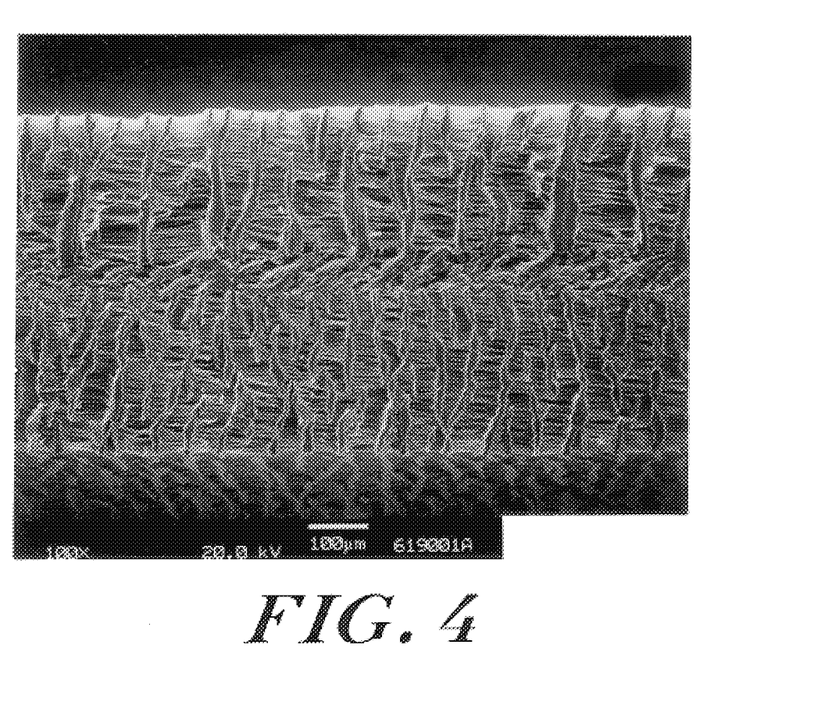
FIG. 4 is a cross-sectional image through a wall of a fourth embodiment of the invention.

Material (B) was radially expanded to a 4 mm ID on a stainless steel forming mandrel, biaxially wound with commercially available PTFE ribbon on a helix winding apparatus, and covered with material (A) that had been previously dilated to a 5 mm ID, restrained to prevent longitudinal shrinkage and placed in an oven at 360° C. for 10 minutes to prepare a lamellate structure (Material B/Biaxial wrap/Material A), a cross-section of which is shown in FIG. 4.

Figure 5:
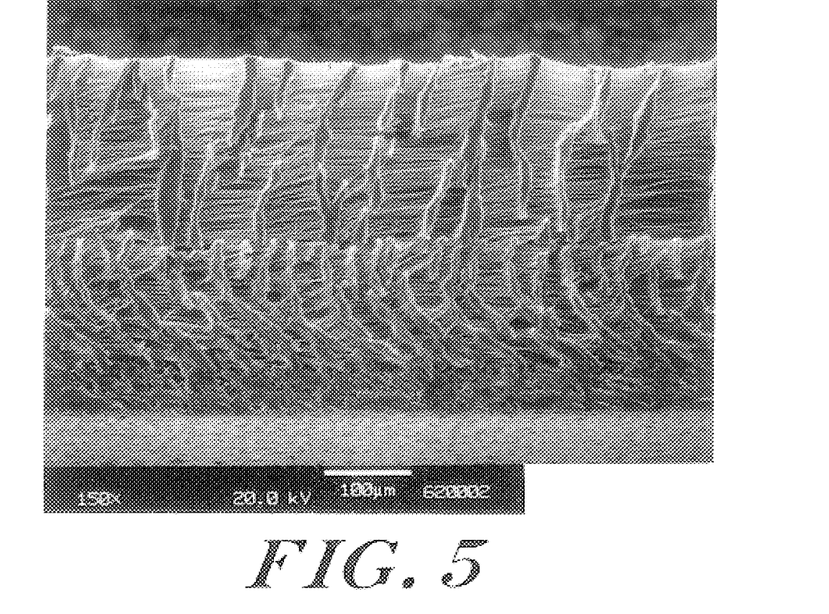
FIG. 5 is a cross-sectional image through a wall of a fifth embodiment of the invention.

PTFE ribbon was biaxially wound onto a stainless steel forming mandrel, covered with material (B) that had been previously dilated to a 5 mm ID, restrained to prevent longitudinal shrinkage and placed in an oven at 360° C. for 5 minutes, to prepare a primary lamellate. The primary lamellate was removed from the oven and allowed to cool, covered with material (A) that had been previously dilated to a 5 mm ID, restrained to prevent longitudinal shrinkage and placed in an oven at 360° C. for 10 minutes to prepare a final lamellate structure (Biaxial ribbon/material B/material A), a cross-section of which is shown in FIG. 5.

Figure 6:
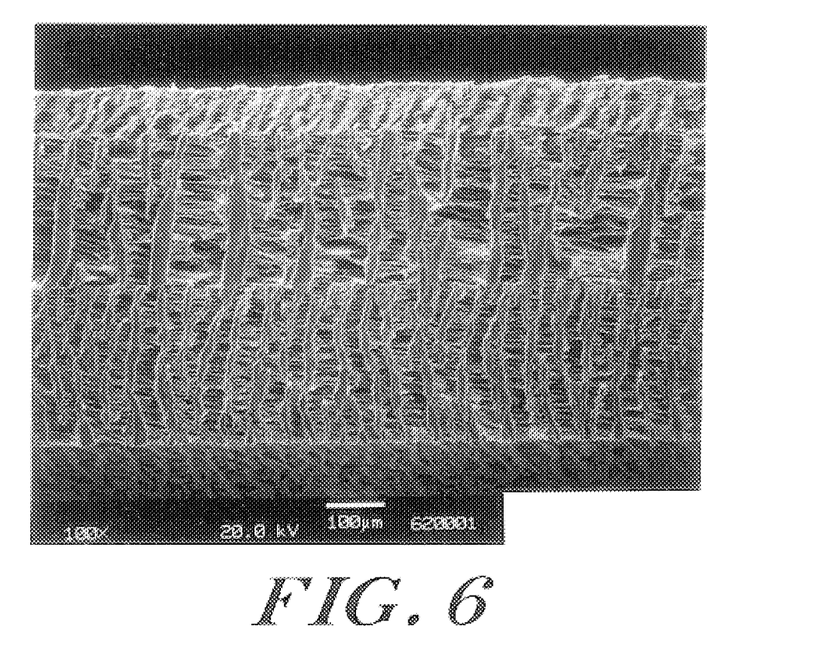
FIG. 6 is a cross-sectional image through a wall of a sixth embodiment of the invention.

Material (B) was radially expanded to a 4 mm ID on a stainless steel forming mandrel, covered with material (A) that had been previously dilated to a 5 mm ID, restrained to prevent longitudinal shrinkage, and placed in an oven at 360° C. for 5 minutes, to prepare a primary lamellate. The primary lamellate was removed from the oven and allowed to cool, covered with a biaxial wrap of PTFE ribbon, restrained to prevent longitudinal shrinkage and placed in an oven at 360° C. for 10 minutes to prepare the final lamellate structure (Material B/Material A/Biaxial ribbon), a cross-section of which is shown in FIG. 6.

EXAMPLE 3

Figure 7:
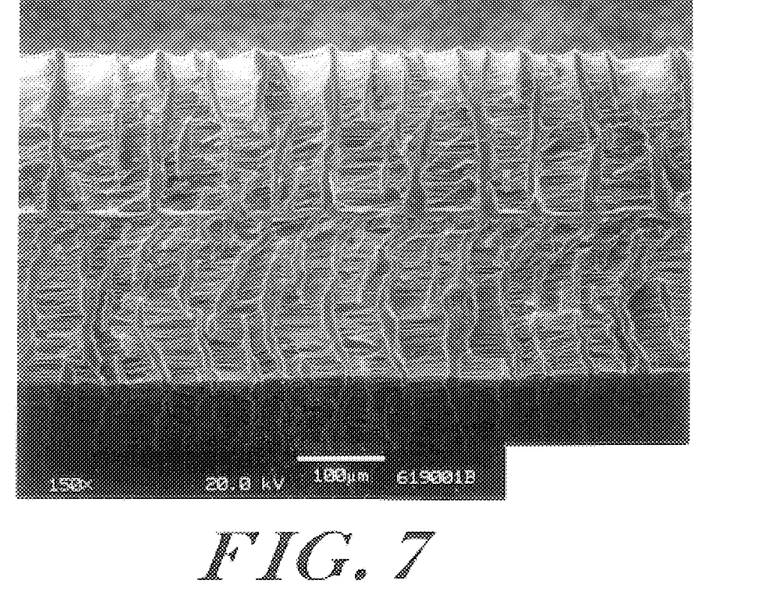
FIG. 7 is a cross-sectional image through a wall of a seventh embodiment of the invention.

Material (B) was radially expanded to a 4 mm ID on a stainless steel forming mandrel, longitudinally wrapped with commercially available PTFE ribbon, and covered with material (A) that had been previously dilated to a 5 mm ID, restrained to prevent longitudinal shrinkage, and placed in an oven at 360° C. for 10 minutes to prepare a lamellate structure (Material B/Longitudinal wrap/Material A), a cross-section of which is shown in FIG. 7.

Figure 8:
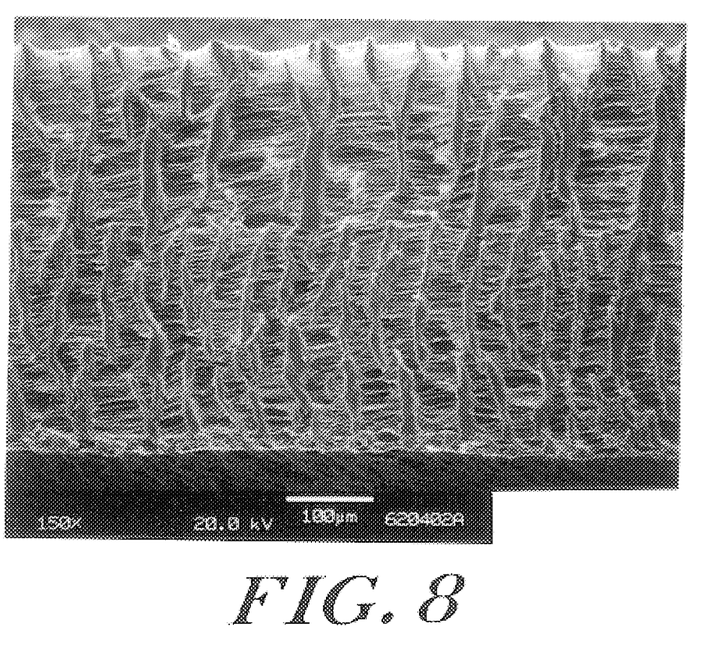
FIG. 8 is a cross-sectional image through a wall of a eighth embodiment of the invention.

PTFE ribbon was placed longitudinally around a stainless steel mandrel, covered with material (B) that had been previously dilated to a 5 mm ID, restrained to prevent longitudinal shrinkage, and placed in an oven at 360° C. for 5 minutes, to prepare a primary lamellate. The primary lamellate was removed from the oven and allowed to cool, covered with material (A) that had been previously dilated to a 5 mm ID, restrained to prevent longitudinal shrinkage and placed in an oven at 360° C. for 10 minutes to prepare a final lamellate structure (Longitudinal ribbon/Material B/Material A), a cross-section of which is shown in FIG. 8.

Figure 9:
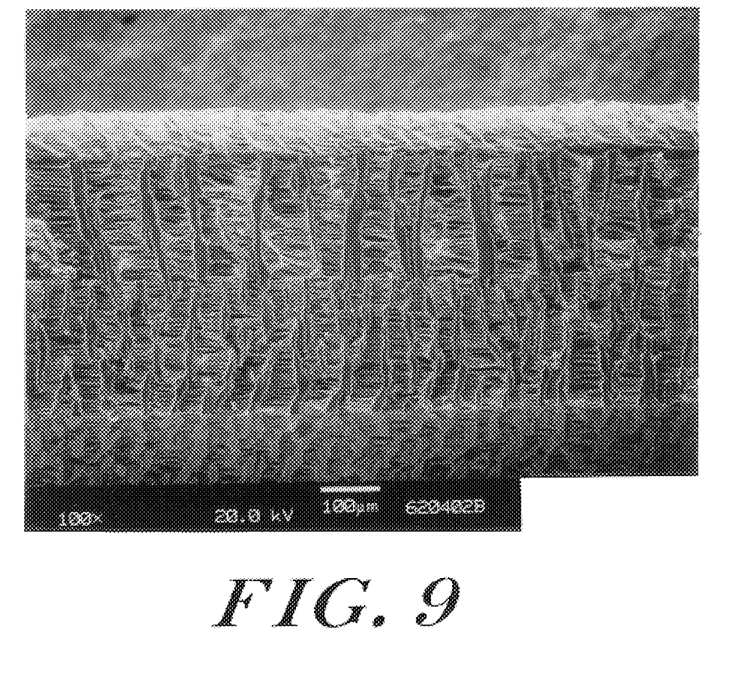
FIG. 9 is a cross-sectional image through the wall of a ninth embodiment of the invention.

Material (B) was radially expanded to a 4 mm ID on a stainless steel forming mandrel, covered with material (A) that had been previously dilated to a 5 mm ID, restrained to prevent longitudinal shrinkage, and placed in an oven at 360° C. for 5 minutes, to prepare a primary lamellate. The primary lamellate was removed from the oven and allowed to cool, covered with a longitudinal wrap of PTFE ribbon, restrained to prevent longitudinal shrinkage and placed in an oven at 360° C. for 10 minutes to prepare a final lamellate structure (Material B/Material A/Longitudinal ribbon), a cross-section of which is shown in FIG. 9.

To assess the in vivo performance of prostheses prepared in this fashion, four millimeter lamellate grafts of various configurations were implanted into the carotid and/or femoral arteries of dogs. Explants were taken at 14, 30, 60, and 180 days. The presence of an intrawall low porosity, high WEP region produced enhanced tissue ingrowth compared to material without such a region, leading applicant to believe that hydraulic forces play a role in the healing process of implantable devices.

The foregoing examples describe the preparation of a tube having enhanced properties as a vascular graft or tissue patch in which a region of high WEP in the wall modulates communication through the wall and the biological response and growth processes occurring in or contiguous to the wall. As such, it provides an improved construction applicable to a broad range of implant and surgical protheses. The invention being thus disclosed, variations and modifications will occur to those skilled in the art and are considered to be within the scope of the invention and its equivalents, as defined by the claims appended hereto.

We claim:
1. A prosthetic member comprising
   a prosthesis wall having at least first, second and third portions along a wall thickness,
   said first portion including a porous inner portion extending continuously along an axis
   said second portion being contiguous to said first portion and forming a barrier impenetrable to cell growth and being permeable with a water entry pressure higher than said first portion
   said third portion lying over said second portion and extending as a continuous body along said axis
   said first, second and third portions being coalesced together to form said wall having cellularly penetrable first and third portions and said second portion modulates cellular penetration of said first and third portions.
2. A prosthetic member according to claim 1, wherein said second portion barrier has a porosity less than fifty micrometers effective to block growth of cells and block transport of large molecules while allowing gases and small soluble molecules to pass through said second portion.

3. A prosthetic member according to claim 1, wherein said first and third portions are continuous tubes and said second portion is a biased wrap.

4. A prosthetic member according to claim 1, wherein said first and third portions are continuous tubes and said second portion is a non-biased wrap.

5. A prosthetic member according to claim 1, wherein said first, second and third portions are each continuous tubes.

6. A prosthetic member according to claim 5, wherein said first and third portions are stretched in at least one direction, and said second portion is substantially unstretched.

7. A prosthetic member according to claim 5, wherein said first and third portions are stretched in a common direction, and said second portion is stretched to form fibrils which are oriented in said second portion across said common direction.

8. A prosthetic member according to claim 1, wherein said second portion barrier has a water entry pressure which prevents weeping after said wall has been wetted.

9. A prosthetic member according to claim 1, wherein said third portion is formed of a porous fluoropolymer having a node and fibril microstructure, wherein the fibrils extend along the axis of said tube and the nodes are oriented to form channels between adjacent nodes, the channels being transverse to said wall and tapering smaller as they extend inwardly.

10. A prosthetic member comprising a prosthesis wall formed entirely of fluoropolymer having at least first, second and third portions along a wall thickness, said first portion including a porous inner section extending continuously along an axis said second portion being contiguous to said first portion and forming a stratum which has a permeability effective for modulating hydrostatic pressure said third portion overlying said second portion and including a porous section extending as a continuous body along said axis said first, second and third portions being coalesced together to form said wall such that the wall has a cellularly penetrable surface and said second portion modulates fluid communication through the wall while preventing cellular growth in said second portion.

11. A prosthetic member comprising an implantable body including a prosthetic wall having first, second and third portions said first portion extending over an area and having a penetrable surface conducive to cellular ingrowth said second portion having a low permeability that allows passage of gas and fluid at a controlled rate, and said third portion having a penetrable surface conducive to cellular ingrowth, said first, second and third portions being arranged along a thickness dimension and coalesced together to form said prosthetic wall as an integral structure of said implantable body to control cellular growth in said first and third portions through modulation by said second portion of transport and fluid communication in the wall.

* * * * *

UNITED STATES PATENT AND TRADEMARK OFFICE
CERTIFICATE OF CORRECTION

PATENT NO. : 5,824,050
DATED : October 20, 1998
INVENTOR(S) : Theodore Karwoski, Paul Martakos, Peter Gingras, Steve A. Herweck, and Tom Swanick It is certified that error appears in the above-identified patent and that said Letters Patent is hereby corrected as shown below:

On the title page, under Inventors, line 1,

Please delete "Hudson" and insert --Hollis--.

Signed and Sealed this

Twenty-third Day of February, 1999

Attest:

Q. TODD DICKINSON

*Attesting Officer*         *Acting Commissioner of Patents and Trademarks*